United States Patent
Cummings et al.

(10) Patent No.: US 7,059,169 B2
(45) Date of Patent: Jun. 13, 2006

(54) FLUID AERATION TEST APPARATUS AND METHOD

(75) Inventors: Jill M. Cummings, Pinckney, MI (US); Christopher C. Morgan, Jr., Rochester Hills, MI (US); Roy Fewkes, Farmington Hills, MI (US); James L. Linden, Rochester Hills, MI (US); Diana Foghel, Dexter, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/776,556

(22) Filed: Feb. 11, 2004

(65) Prior Publication Data

US 2005/0172698 A1    Aug. 11, 2005

(51) Int. Cl.
*G01N 7/00* (2006.01)
*G01N 9/00* (2006.01)
*G01N 33/18* (2006.01)
*G01N 33/26* (2006.01)

(52) U.S. Cl. ............... 73/19.01; 73/19.1; 73/19.11; 73/32 R; 73/32 A; 73/53.01; 73/53.05; 73/61.41

(58) Field of Classification Search ............... 73/19.01, 73/19.1, 19.11, 32 R, 53.01, 32 A, 53.05, 73/60.11, 61.41, 61.44
See application file for complete search history.

(56) References Cited

U.S. PATENT DOCUMENTS

| | | | | |
|---|---|---|---|---|
| 3,497,034 A | * | 2/1970 | Eddy, Jr. | 184/109 |
| 4,584,866 A | * | 4/1986 | Janssen | 73/19.1 |
| 5,375,459 A | * | 12/1994 | Gerke et al. | 73/60.11 |
| 5,902,487 A | * | 5/1999 | Pickering et al. | 210/709 |
| 5,965,805 A | | 10/1999 | Watts et al. | 73/53.01 |
| 2003/0096719 A1 | * | 5/2003 | Hasegawa et al. | 510/141 |
| 2003/0167824 A1 | * | 9/2003 | Brown et al. | 73/32 A |

FOREIGN PATENT DOCUMENTS

WO     WO 01/30174     *  5/2001  ............... 426/474

OTHER PUBLICATIONS

Colby et al, "Determination of the Air Entrainment Characteristics of Automatic Transmission Fluids Using a Dynamic Flow Apparatus," SAE Technical Paper 982669.
Dixon et al, "Foaming and Air Entrainment in Automatic Transmission Fluids," SAE Technical Paper 760575.
Koch et al, "Oil Aeration in Combustion Engines—Analysis and Optimization," SAE Technical Paper 2001-01-1074.

(Continued)

*Primary Examiner*—Daniel S. Larkin
(74) *Attorney, Agent, or Firm*—Christopher DeVries

(57) ABSTRACT

A test apparatus for measuring the air entrainment characteristics of a fluid includes a reservoir for containing the fluid, an aerator apparatus to cause air entrainment of the fluid, and a density meter to measure the effects of air entrainment on fluid density. The test apparatus enables in-situ measurement of the transient air entrainment behavior of the fluid. A corresponding method is provided.

14 Claims, 3 Drawing Sheets

OTHER PUBLICATIONS

Mitarai et al, "The Circulation Type Foaming Test Method of Lubricating Oils to Simulate the Foaming Characteristics of ATF in the Automatic Transmission," SAE Technical Paper 2002-01-2818.

Nemoto et al, "A Study of Engine Oil Aeration," JSAE Review 18 (1997), 271-276.

Zander et al, "A Laboratory Method for the Evaluation of Air Release Behaviour of Liquid Lubricants," CEC Paper 97-T202.

"Standard Test Method for Air Release Properties of Petroleum Oils," ASTM D3427—96, pp. 435-438.

"Standard Test Method for Foaming Characteristics of Lubricating Oils," ASTM D892—95, pp. 277-282.

* cited by examiner

FLUID AERATION TEST APPARATUS AND METHOD

TECHNICAL FIELD

This invention relates to fluid aeration test apparatuses and methods that employ density meters to enable measurement of transient air entrainment characteristics of fluids.

BACKGROUND OF THE INVENTION

In various mechanical devices, such as automatic transmissions, a fluid is circulated as a coolant, a lubricant, and to transmit force, e.g., as a hydraulic fluid to apply clutches. Typically, the fluid contains a base oil and additives to provide the fluid with certain performance properties for a given fluid application. During circulation in an automatic transmission, fluid from a sump is pressurized by a pump, circulated through tubes, valves, and orifices, etc., and then allowed to drain back into the sump. During circulation, the fluid is agitated and exposed to air, and as a result, air becomes entrained in the fluid.

Air entrainment is undesirable for several reasons. First, entrained air can chemically degrade the fluid, causing it to lose its desirable functional characteristics. Entrained air contains water vapor, nitrogen, and oxygen, which can degrade the carbon chain molecules of the base oil and the additives. For example, oxygen can change the base oil into a hydroperoxide, an alcohol, or an acid.

Second, entrained air is compressible; thus, the fluid with entrained air may not respond as desired when transmitting a force as a hydraulic fluid due to natural frequency and bulk modulus changes. Third, entrained air will also compromise the fluid film strength thus reducing the fluid's lubricity.

Due to air entrainment's negative effects, it is desirable to utilize fluids in automatic transmissions and other mechanical devices that are formulated to meet predetermined air entrainment criteria, e.g., the amount of air entrained in the fluids must be less than a predetermined amount after significant agitation and exposure to air. The prior art includes various air entrainment test apparatuses and methods used to determine a fluid's suitability in a particular application. Typically, the prior art apparatuses and methods involve agitating the fluid to cause exposure to air, and then determining the amount of air entrainment by measuring the volume of the fluid or attempting to separate the entrained air from the fluid. Such techniques are time consuming and severely limit the frequency of measurement. Prior art air entrainment test apparatuses and methods are deficient in that they fail to, or are unable to, measure the transient air entrainment characteristics of a fluid such as rates of air entrainment or disentrainment after a change in the amount or intensity of agitation. For example, prior art test apparatuses cannot measure and calculate air entrainment data from the first few seconds following a change in agitation, nor during agitation.

SUMMARY OF THE INVENTION

A test apparatus for determining air entrainment characteristics of a fluid includes a reservoir for containing the fluid, and an aerator apparatus operatively connected to the reservoir and configured to selectively aerate the fluid, thereby to cause the fluid to undergo a transient air entrainment response period wherein the amount of air entrained in the fluid varies with respect to time. A density meter is operatively connected to the reservoir and configured to measure the density of the fluid at a plurality of time values during the transient air entrainment response period. The use of a density meter to measure air entrainment provides increased accuracy compared to the prior art. For example, prior art test apparatuses require assumptions about the equilibrium, nonaerated fluid air content. The density meter eliminates the need for such assumptions by allowing a test apparatus operator to isolate the fluid density effects caused by air entrainment. The use of a density meter also improves upon the prior art by enabling in-situ, substantially instantaneous density measurements at any point during testing. Accordingly, the frequency of measurement possible with the density meter, i.e., the number of measurements obtained per unit time, is substantially higher than the prior art.

In a preferred embodiment, the test apparatus includes a temperature control device, such as a heating element, configured to selectively heat the fluid according to known operating conditions of a transmission, and a control apparatus configured to selectively control the aerator apparatus and the temperature control device according to a predetermined algorithm or test protocol. The test apparatus is thus automated to reduce operator influence on test results compared to the prior art.

The control apparatus is preferably configured to record the density of the fluid at each of a plurality of time values during the transient air entrainment response period. The test apparatus thus improves upon the prior art by providing information about the transient air entrainment response of the fluid. Characteristics such as the rate of air entrainment and the rate of air disentrainment can be determined from the information provided by the test apparatus of the present invention. Knowledge of such characteristics is particularly important in light of the relatively short residence time of fluid in automatic transmission sumps.

A corresponding method for determining air entrainment characteristics of a fluid is also provided. The method includes aerating the fluid for a first predetermined time period, including a first transient response period, and generating a set of data by recording a corresponding measured density of the fluid for each of a plurality of time values within the first transient response period. Preferably, the method also includes allowing the fluid to deaerate, i.e., allowing the fluid to release entrained air, for a second predetermined time period including a second transient response period, and recording a corresponding measured density of the fluid for each of a plurality of time values within the second transient response period to further generate the set of data. The fluid is preferably maintained at a substantially constant temperature during the first and second predetermined time periods so that the data set correlates to the air entrainment behavior of the fluid at a single temperature. The method can be repeated with the fluid maintained at other temperatures to obtain data sets describing the air entrainment behavior of the fluid at the other temperatures.

The above features and advantages, and other features and advantages, of the present invention are readily apparent from the following detailed description of the best mode for carrying out the invention when taken in connection with the accompanying drawings.

DESCRIPTION OF THE PREFERRED EMBODIMENT

Figure 1:
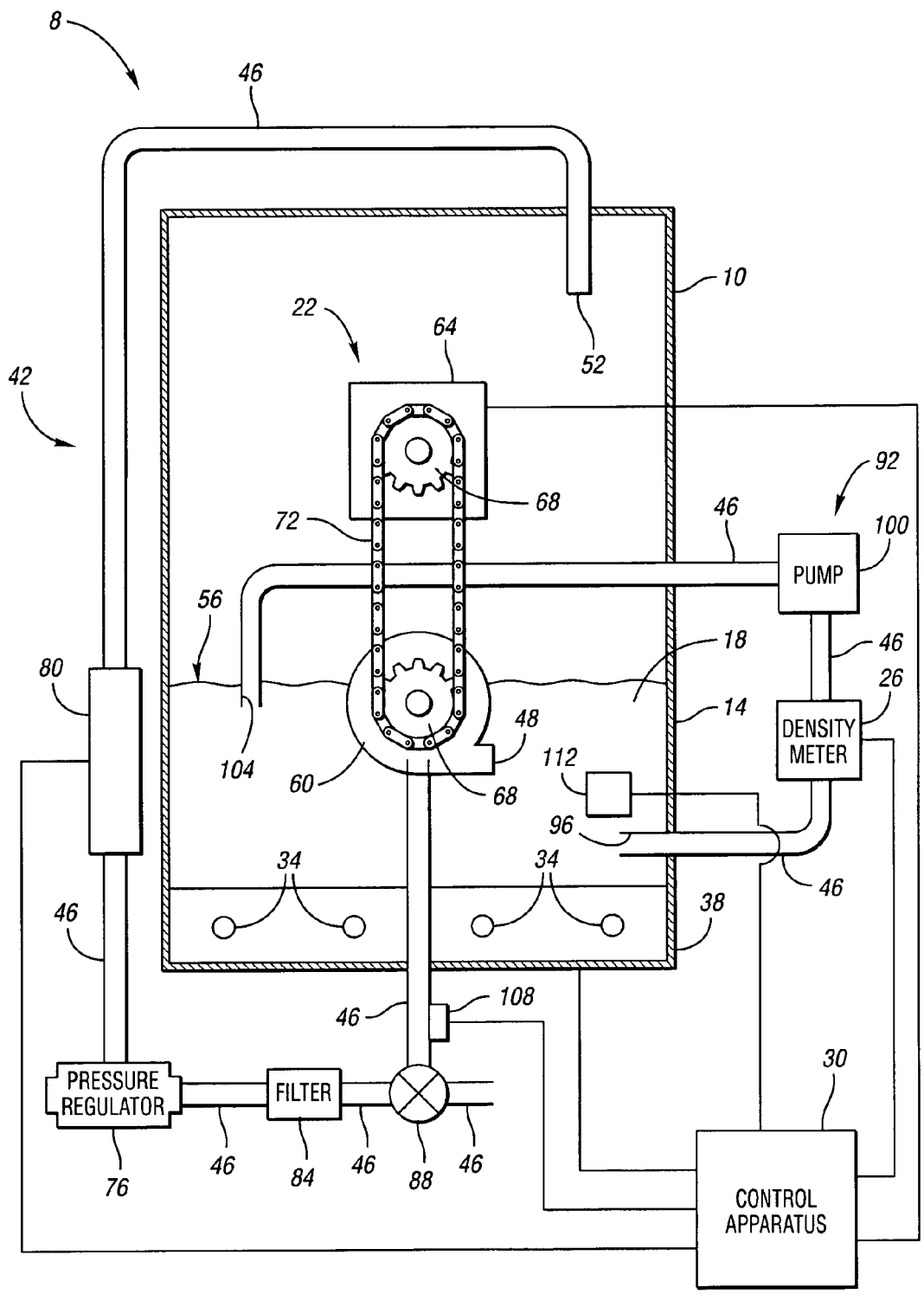
FIG. 1 is a schematic front view of a fluid test apparatus according to the claimed invention.

Referring to FIG. 1, an aeration test apparatus 8 is schematically depicted. The test apparatus 8 includes an aluminum box 10 that forms a reservoir 14 for a fluid 18 undergoing testing. The test apparatus 8 also includes an aerator apparatus 22 operatively connected to the reservoir 14 and configured to aerate the fluid 18, thereby to cause air entrainment of the fluid. In the context of the present invention, to "aerate" means to "expose to the action or effect of air" or to "introduce air into a fluid." "Air entrainment" is an effect of aeration. The fluid 18 undergoes a transient response period, during which the amount of entrained air varies with respect to time, before reaching a quasi-steady-state condition wherein, with constant testing parameters, the amount of entrained air remains substantially constant. A density meter 26 is operatively connected to the reservoir 14 and configured to selectively measure the density of the fluid 18 and thereby obtain an indication of the amount of air entrained therein. A control apparatus 30 is operatively connected to the density meter 26 for selectively recording the density of the fluid with sufficient frequency to indicate transient air entrainment characteristics of the fluid such as rate of air entrainment and time to reach steady state or maximum air entrainment.

The test apparatus 8 includes temperature control devices, such as heating elements 34 inside the baseplate 38 of the box 10. The heating elements 34 are sufficiently configured and positioned with respect to the reservoir 14 to selectively heat the fluid 18 without contacting the fluid.

The aerator apparatus 22 includes a first hydraulic circuit 42. The first hydraulic circuit 42 includes tubes 46 at least partially defining a conduit through which the fluid flows. The circuit 42 includes an inlet 48 and an outlet 52 located inside the box 10. The outlet 52 is at an elevation higher than the inlet 48 such that, when fluid 18 is added to the reservoir 14 for testing, the inlet is below the surface 56 of the fluid 18, and the outlet 52 is above the surface 56 of the fluid 18. A primary pump 60 is employed to pressurize the fluid 18 so that it is drawn into the inlet 48 and directed through the circuit 42. The primary pump 60 in a preferred embodiment is located within the reservoir 14 such that the fluid level, i.e., the surface of the fluid, is above the midpoint of the primary pump to simulate drawing fluid from a sump in an automatic transmission. The primary pump 60 is powered by an electric motor 64 via sprockets 68 interconnected by a chain drive 72. The chain drive 72 is positioned such that it is at least partially submerged beneath the surface 56 of the fluid to agitate the surface and thereby cause aeration of the fluid.

The fluid in the first hydraulic circuit 42 is pumped through a pressure regulator 76 to control line pressure, a heat exchanger 80, and the outlet 52 from which it returns to the reservoir 14. The placement of the outlet 52 above the surface 56 of the fluid 18 in the reservoir causes further aeration and simulates the flow of automatic transmission fluid into a sump. The inlet 48 and the outlet 52 are preferably selectively repositionable so that an operator can adjust the location and orientation of the inlet and the outlet. The temperature of the fluid returning to the reservoir is affected by the heat exchanger 80, which is controlled by adjusting the flow of water through the heat exchanger via a valve (not shown). The first hydraulic circuit preferably includes a filter 84 and an air release valve 88 and drain.

The density meter 26 is part of a second hydraulic circuit 92. The second hydraulic circuit 92 includes tubes 46 at least partially defining a conduit through which the fluid flows. Fluid 18 is drawn to the density meter 26 from the reservoir 14 through an inlet 96. In the preferred embodiment, the density meter 26 is a Coriolis mass flow/density meter. A secondary pump 100 downstream from the density meter 26 pumps the fluid through the second hydraulic circuit 92. The second hydraulic circuit 92 includes an outlet 104 through which fluid is returned to the reservoir 14.

It may be desirable for the apparatus to include a secondary density measurement device. For example, a liquid density sinker may be suspended by a platinum or titanium wire from a scale into the reservoir 14 such that it is at least partially submerged in the fluid 18. The fluid density may then be calculated by subtracting the dry weight of the sinker and wire from the observed weight of the sinker and wire suspended in the fluid 18 before and after agitation, and dividing by the volume of the sinker. Titanium or platinum wire is preferably employed to minimize buoyancy effects.

Similarly, a gas tight syringe (not shown) may be connected to a tube 46 in the second hydraulic circuit 92 prior to the density meter 26 to observe the amount of air entrained in the fluid. A volume of the fluid may be drawn into the gas tight syringe and exposed to a partial vacuum to release the entrained air in the fluid sample. The volume of the fluid after the release of entrained air is subtracted from the volume of the fluid prior to the release of the entrained air to obtain the total air volume contained in the fluid.

The control apparatus 30 is operatively connected to several sensors that monitor, and transmit signals indicative of, fluid conditions within the test apparatus 8. More specifically, the control apparatus 30 is operatively connected to a pressure transducer 108 in the first hydraulic circuit 42 that transmits signals indicative of the pressure in the first hydraulic circuit 42 to the control apparatus 30, and a temperature sensor 112 in the reservoir 14 that transmits signals indicative of the temperature of the fluid 18 to the control apparatus 30.

The control apparatus 30 is also configured to control test parameters, including fluid temperature and pressure. More specifically, the control apparatus 30 is connected to the heating elements 34 and the heat exchanger 80 to control fluid temperature, and to the electric motor 64 to selectively control the speed of the primary pump 60, and, correspondingly, the fluid pressure and the fluid mass flow rate through the first hydraulic circuit 42. The pump speed affects the amount and rate of fluid aeration through two mechanisms. First, the speed of the chain drive 72 increases with electric motor speed, resulting in increased agitation of the surface 56 of the fluid 18. Second, the flow rate of fluid through the outlet 52, where it is aerated as it falls into the reservoir, increases with pump speed.

Figure 2:
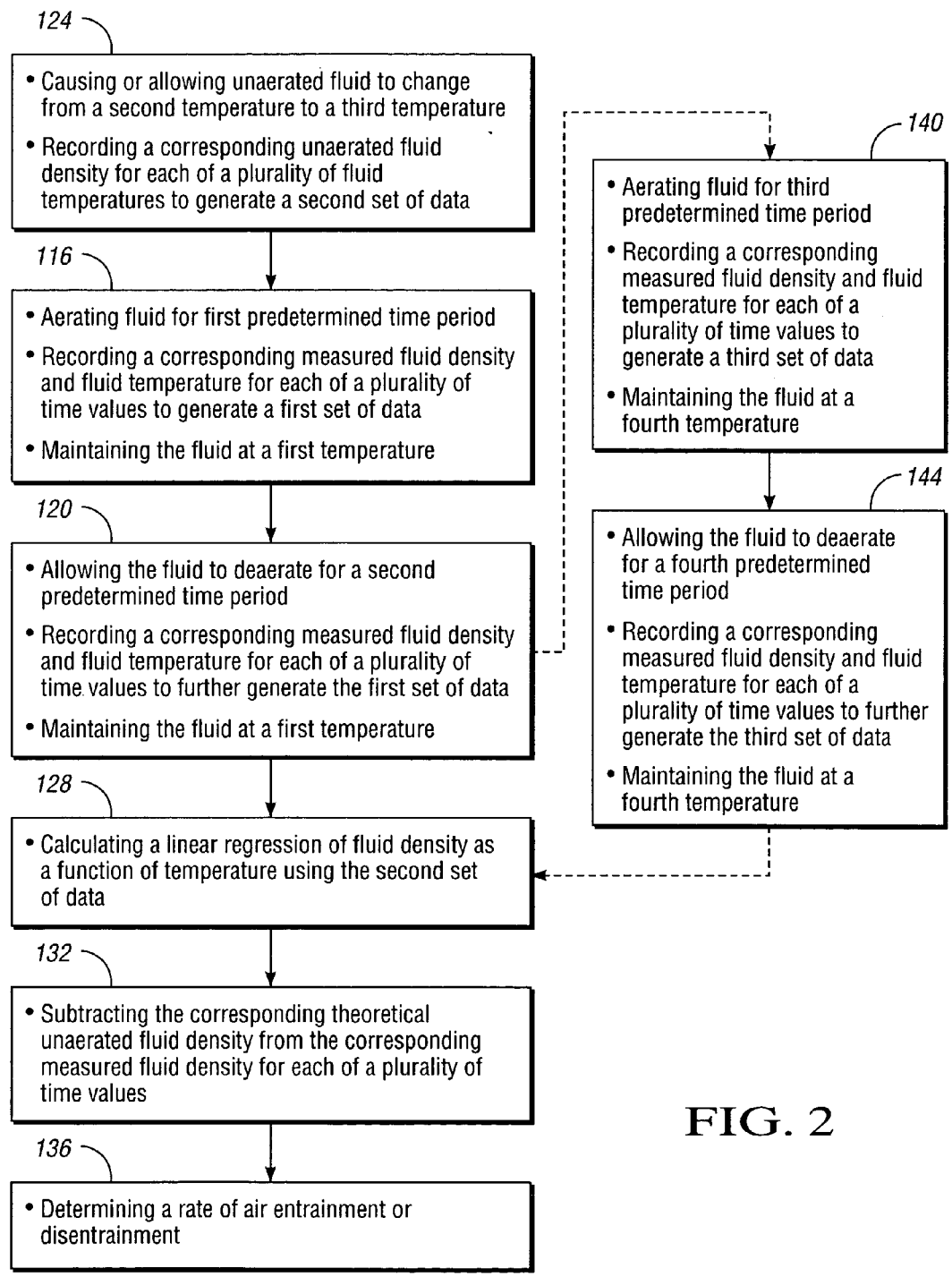
FIG. 2 is a flowchart depiction of a method for determining air entrainment characteristics of a fluid.

The control apparatus 30 is preferably programmable to vary the test parameters according to a predetermined test protocol in order to observe the fluid's air entrainment characteristics under varying conditions. Referring to FIG. 2, a preferred test protocol and method is schematically depicted.

The method includes an aeration data acquisition step 116 which includes aerating the fluid for a first predetermined time period, such as 30 minutes, and generating a first set of data by recording a corresponding measured density of the fluid for each of a plurality of time values within the first predetermined time period. Aerating the fluid is performed by operating the primary pump at a speed sufficient to cause significant agitation of the fluid during exposure to air. Generating the first set of data is preferably performed by the control apparatus recording the density of the fluid as measured by the density meter at a rate of 5 Hz, i.e., once every 0.2 seconds, during the first predetermined time period. The control apparatus preferably records the corresponding density for each of the plurality of time values to random access memory (RAM) or a temporary storage medium, such as a hard drive, where it is accessible for processing.

Aerating the fluid during the first predetermined time period results in a first transient response period wherein the air entrainment of the fluid varies with respect to time. The frequency of fluid density measurement and recording is sufficiently high so that data describing the behavior of the fluid during the first transient response period is obtained. Accordingly, the step of generating a first set of data includes recording a corresponding measured density of the fluid for each of a plurality of time values within the first transient response period.

The fluid is preferably substantially unaerated at the initiation of the first predetermined time period. The fluid is characterized by a maximum possible amount of air entrainment for a given set of test parameters. In order to determine such fluid characteristics as the time until maximum possible air entrainment, the step of aerating the fluid preferably causes the fluid to reach the maximum possible amount of air entrainment.

In order to determine such fluid characteristics as the rate of air disentrainment, i.e., the rate at which entrained air is released from the fluid, the method preferably includes a deaeration data acquisition step 120. Step 120 includes allowing the fluid to deaerate for a second predetermined time period to result in a second transient response period wherein the air entrainment of the fluid varies with respect to time, and recording a corresponding measured density of the fluid for each of a plurality of time values within the second time period, including within the second transient response period, to further generate the first data set.

The density of the fluid is a function of both the amount of air entrainment and the temperature of the fluid. In some cases, it may be desirable to isolate the density effects of air entrainment from the density effects of temperature. Accordingly, generating the first set of data preferably includes recording a corresponding measured temperature of the fluid for each of the plurality of time values. Preferably, the fluid is maintained at a first temperature during steps 116 and 120, in which case recording a corresponding measured temperature of the fluid may simply comprise recording the first temperature once.

In order to isolate the density effects of air entrainment from the density effects of temperature, the method further includes determining a corresponding theoretical unaerated fluid density for each of the plurality of time values in the first set of data. In the preferred embodiment, determining a corresponding theoretical unaerated fluid density for each of the plurality of time values in the first set of data includes a temperature-density data acquisition step 124, and a data processing step 128. The temperature-density data acquisition step is preferably performed prior to step 116, and includes causing or allowing the fluid to change from a second temperature to a third temperature in an unaerated state, and generating a second set of data by recording a corresponding measured fluid density for each of a plurality unaerated fluid temperatures between the second and third temperatures. The data processing step 128 includes calculating a mathematical representation, such as a linear regression, of fluid density as a function of temperature using the second set of data. The corresponding theoretical unaerated fluid density for each time value in the first data set is then determined by using the corresponding measured temperature and the mathematical representation.

Figure 3:
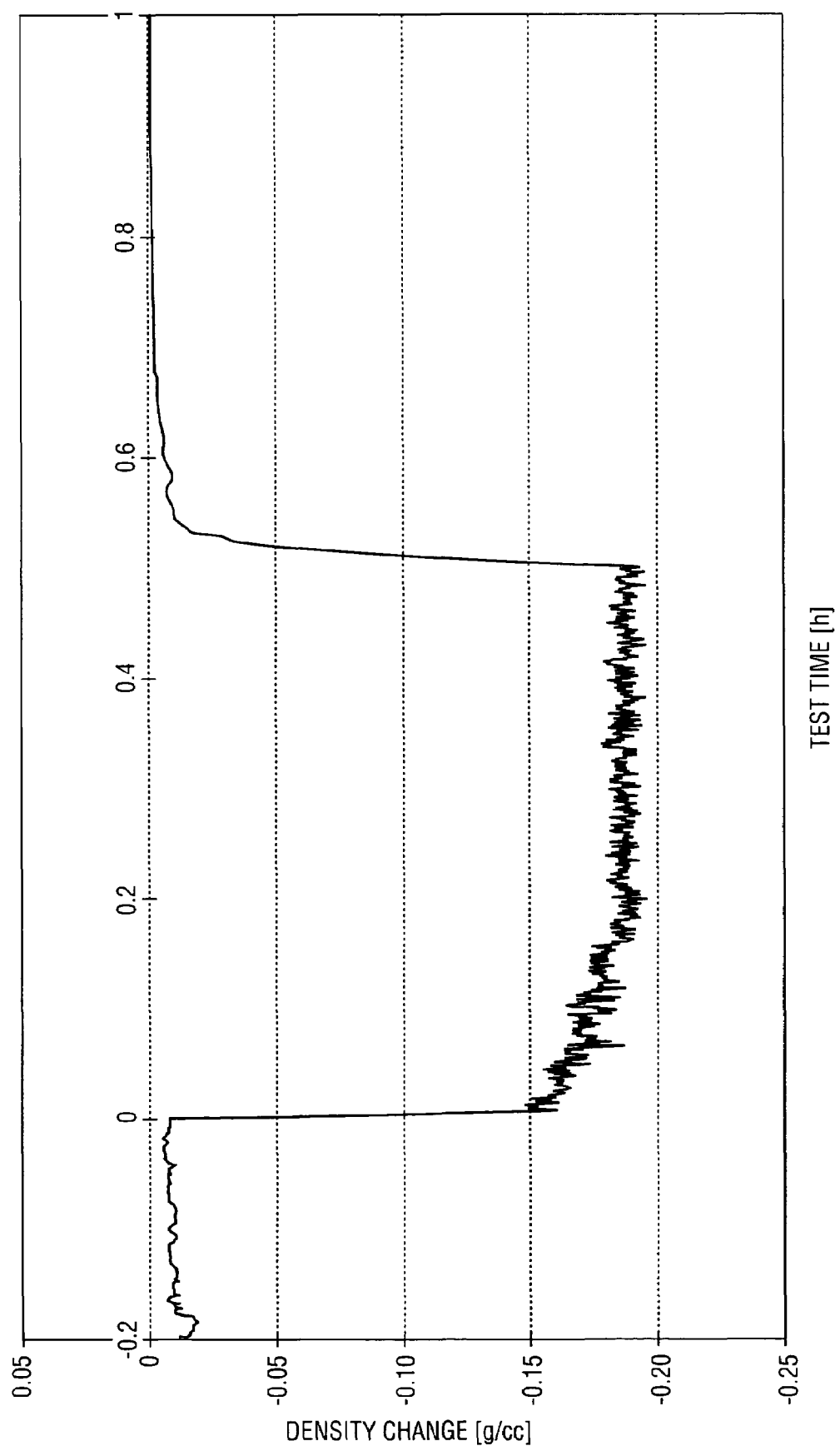
FIG. 3 is a graphical depiction of sample data derived from the method depicted in FIG. 2.

Isolating the effects of air entrainment on density is completed by generating a profile describing the effect of air entrainment on fluid density for each of the plurality of time values. This is accomplished by determining, for each time value, the difference between the corresponding theoretical unaerated fluid density value and the corresponding measured fluid density value to obtain a corresponding density change as a result of air entrainment 132. FIG. 3 depicts a sample profile describing the effect of air entrainment on fluid density for a plurality of time values in graphical form.

The data thus obtained can be advantageously used to determine transient air entrainment characteristics of the fluid. Accordingly, the method may further include determining a rate of air entrainment 136, such as the amount of time from the beginning of the first predetermined time period to when the fluid reaches maximum air entrainment, or, if the fluid is at the maximum possible air entrainment at the beginning of the second predetermined time period and becomes substantially unaerated within the second time period, the amount of time from the beginning of the second predetermined time period until the fluid is substantially unaerated. A preferred method of determining the point of maximum possible air entrainment is to determine when the first derivative of the data plotted in FIG. 3 is substantially zero, for example, when the slope is +/−0.005 g/cm$^3$/minute for two consecutive measurements after the first transient response period. In a preferred embodiment, a fluid is considered substantially unaerated when the density change is +/−0.0015 g/cm$^3$.

It may be desirable to repeat the process at a variety of different fluid temperatures, depending on the intended operating conditions for the fluid being tested. Accordingly, the method may also include aerating the fluid for a third predetermined time period including a third transient response period in which the air entrainment of the fluid varies with respect to time 140; allowing the fluid to deaerate for a fourth predetermined time period including a fourth transient response period in which the air entrainment of the fluid varies with respect to time 144; substantially maintaining the fluid at a fourth temperature different from the first temperature during the third and fourth predetermined time periods 140, 144; and generating a second set of data by recording a corresponding measured fluid density for each of a plurality of time values in the third and fourth predetermined time periods 140, 144.

While the best mode for carrying out the invention has been described in detail, those familiar with the art to which this invention relates will recognize various alternative designs and embodiments for practicing the invention within the scope of the appended claims.

The invention claimed is:

1. A test apparatus for determining air entrainment characteristics of a fluid, the test apparatus comprising:
    a reservoir for containing the fluid;
    an aerator apparatus operatively connected to the reservoir and configured to selectively aerate the fluid and thereby cause the fluid to undergo a transient air entrainment response period wherein the amount of air entrained in the fluid varies with respect to time;
    a density meter operatively connected to the reservoir and configured to measure the density of the fluid at each of a plurality of time values during the transient air entrainment response period;

a heating element sufficiently positioned with respect to the reservoir to selectively heat the fluid; and a control apparatus operatively connected to the density meter and configured to record the density of the fluid a plurality of times during the transient air entrainment response period.

2. The test apparatus of claim 1, wherein the aerator apparatus includes a hydraulic circuit with an inlet in the reservoir and an outlet in the reservoir, the outlet being positionable above the inlet so that the inlet may be below the surface of the fluid and the outlet may be above the surface of the fluid; and wherein the aerator apparatus includes a pump configured to cause the fluid to circulate through the hydraulic circuit.

3. The test apparatus of claim 1, wherein the density meter is a Coriolis density meter.

4. A test apparatus for determining air entrainment characteristics of a fluid, the test apparatus comprising:

a reservoir for containing the fluid;

an aerator apparatus operatively connected to the reservoir and configured to selectively aerate the fluid and thereby cause the fluid to undergo a transient air entrainment response period wherein the amount of air entrained in the fluid varies with respect to time;

a density meter operatively connected to the reservoir and configured to measure the density of the fluid at each of a plurality of time values during the transient air entrainment response period;

a hydraulic circuit with an inlet in the reservoir and an outlet being positionable above the inlet so that the inlet may be below the surface of the fluid and the outlet may be above the surface of the fluid; and wherein the aerator apparatus includes a pump configured to cause the fluid to circulate through the hydraulic circuit;

a programmable control apparatus operatively connected to the pump and configured to selectively control the pump to affect the pressure of the fluid in the hydraulic circuit; and a heating element sufficiently positioned with respect to the reservoir to selectively heat the fluid.

5. The test apparatus of claim 4, wherein the control apparatus is operatively connected to the heating element and configured to selectively control the heating element to affect the temperature of the fluid.

6. A method of determining air entrainment characteristics of a fluid, the method comprising:

aerating the fluid for a first predetermined time period to result in a first transient response period in which the air entrainment of the fluid varies with respect to time; and generating a first set of data by recording a corresponding measured density of the fluid for each of a plurality of time values within the first transient response period;

wherein the fluid is substantially unaerated at the initiation of the first predetermined time period, wherein the fluid is characterized by a maximum possible amount of air entrainment; and wherein said aerating the fluid causes the fluid to reach the maximum possible amount of air entrainment.

7. A method of determining air entrainment characteristics of a fluid, the method comprising:

aerating the fluid for a first predetermined time period to result in a first transient response period in which the air entrainment of the fluid varies with respect to time;

generating a first set of data by recording a corresponding measured density of the fluid for each of a plurality of time values within the first transient response period;

allowing the fluid to deaerate for a second predetermined time period to result in a second transient response period wherein the air entrainment of the fluid varies with respect to time; and wherein said generating a first set of data includes recording a corresponding measured density of the fluid for each of a plurality of time values within the second transient response period.

8. The method of claim 7, wherein said generating a first set of data includes recording a corresponding temperature of the fluid for each of the plurality of time values.

9. The method of claim 8, further comprising:

determining a corresponding theoretical unaerated fluid density for each of the plurality of time values in the first set of data using the corresponding measured fluid temperature; and isolating the density effects of air entrainment from the density effects of temperature by, for each of the plurality of time values in the first set of data, determining the difference between the corresponding theoretical unaerated fluid density and the corresponding measured fluid density.

10. The method of claim 9, wherein said determining a corresponding theoretical unaerated fluid density for each of the plurality of time values in the first set of data includes:

causing or allowing the fluid to change from a first temperature to a second temperature in an unaerated state; and generating a second set of data by recording a corresponding measured fluid density for each of a plurality unaerated fluid temperatures.

11. The method of claim 10, wherein said determining a corresponding theoretical unaerated fluid density for each of the plurality of time values in the first set of data further includes calculating a mathematical representation of fluid density as a function of temperature using the second set of data.

12. The method of claim 9, further comprising determining a rate of air entrainment or disentrainment.

13. The method of claim 7, further comprising substantially maintaining the fluid at a first temperature during the first and second predetermined time periods;

aerating the fluid for a third predetermined time period including a third transient response period in which the air entrainment of the fluid varies with respect to time;

allowing the fluid to deaerate for a fourth predetermined time period including a fourth transient response period in which the air entrainment of the fluid varies with respect to time;

substantially maintaining the fluid at a second temperature different from the first temperature during the third and fourth predetermined time periods; and generating a second set of data by recording a corresponding measured fluid density for each of a plurality of time values in the third and fourth predetermined time periods.

14. A method for determining air entrainment characteristics of a fluid, the method comprising:

aerating the fluid to cause a first transient response period wherein the air entrainment of the fluid varies with respect to time;

allowing the fluid to deaerate to result in a second transient response period wherein the air entrainment of the fluid varies with respect to time;

generating a set of data by recording a corresponding measured density of the fluid for each of a plurality of time values within the first transient response period and within the second transient response period;

determining a corresponding theoretical unaerated fluid density for each of the plurality of time values in the set of data; and subtracting, for each of the plurality of time values in the set of data, the corresponding theoretical unaerated fluid density from the corresponding measured fluid density to isolate the density effects of air entrainment from the density effects of temperature.

* * * * *